United States Patent [19]

Jones

[11] 4,272,429

[45] Jun. 9, 1981

[54] THERMALLY STABLE, FLAME-RETARDANT POLYMERS AND SELECTED OLIGOMERS USEFUL THEREIN

[75] Inventor: Richard H. Jones, Newark, Del.

[73] Assignee: E. I. Du Pont de Nemours and Company, Wilmington, Del.

[21] Appl. No.: 125,849

[22] Filed: Feb. 29, 1980

Related U.S. Application Data

[63] Continuation-in-part of Ser. No. 35,097, May 1, 1979, abandoned.

[51] Int. Cl.$^3$ ............................ C08K 7/14; C08K 5/06
[52] U.S. Cl. ............................ 260/37 N; 260/45.95 G; 568/637; 568/649
[58] Field of Search ............ 260/45.95 G, 37 N, 40 R; 568/637, 649

[56] References Cited

U.S. PATENT DOCUMENTS

| | | | |
|---|---|---|---|
| 3,076,784 | 2/1963 | Huermann et al. | 260/47 |
| 3,355,272 | 11/1967 | D'Alessandro | 51/298 |
| 3,395,120 | 7/1968 | Bremmer et al. | 260/47 |
| 3,532,759 | 10/1970 | Schnell et al. | 260/45.95 G |
| 3,755,467 | 8/1973 | Darsow et al. | 260/613 R |
| 3,760,003 | 9/1973 | Asadorian et al. | 260/45.95 G |
| 3,929,901 | 12/1975 | Darsow et al. | 260/45.95 G |
| 3,989,531 | 11/1976 | Orlando et al. | 260/45.95 G |
| 4,141,880 | 2/1979 | Nametz | 260/37 N |

FOREIGN PATENT DOCUMENTS

| | | |
|---|---|---|
| 2021830 | 11/1970 | Fed. Rep. of Germany . |
| 2432833 | 1/1976 | Fed. Rep. of Germany . |
| 2659537 | 7/1978 | Fed. Rep. of Germany . |
| 2369312 | 6/1978 | France . |
| 48-49832 | 7/1973 | Japan . |
| 51-117737 | 10/1976 | Japan . |
| 51-73548 | 6/1978 | Japan . |
| 53-065353 | 6/1978 | Japan . |
| 53-038759 | 10/1978 | Japan . |

*Primary Examiner*—V. P. Hoke

[57] ABSTRACT

Oligomers of aromatic diols and brominated diphenyl compounds are described. They are useful in resin blends with thermoplastic polymers to impart flame-retardancy thereto without substantial resin degradation at molding temperatures.

5 Claims, No Drawings

THERMALLY STABLE, FLAME-RETARDANT POLYMERS AND SELECTED OLIGOMERS USEFUL THEREIN

CROSS-REFERENCE TO RELATED APPLICATIONS

This application is a continuation-in-part of application Ser. No. 35,097, filed May 1, 1979, now abandoned.

FIELD OF THE INVENTION

This invention relates to oligomers of aromatic diols and brominated diphenyl compounds, and to flame-retardant resins containing them.

BACKGROUND OF THE INVENTION

Heretofore, brominated compounds have been employed in thermoplastic polymers to make resins which have improved flame-retardance over the thermoplastic polymer alone. However, many such brominated compounds, such as decabromodiphenyl ether, tend to degrade these polymers at melt-processing temperatures, and to migrate in articles molded from the resin toward the surface of the molded article.

New brominated oligomers have now been discovered which when employed with thermoplastic polymers result in flame-retardant molding blends which have better stability toward thermal degradation than do resins which contain some known brominated flame-retardants. Moreover, the new oligomers do not exhibit any substantial tendency to migrate toward the surface of articles molded from the resins.

SUMMARY OF THE INVENTION

The new oligomers are represented by the formula

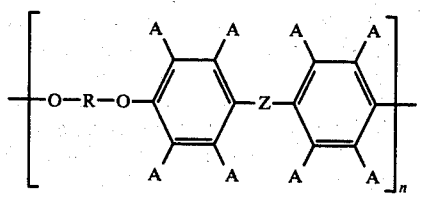

wherein R is a divalent arylene group of between about 6-15 carbon atoms, and preferably is

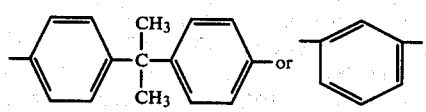

Z is O, S,

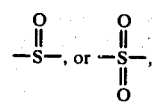

each A is independently hydrogen or bromine with the proviso that at least six of the A groups are bromine; and n is a cardinal number of between about 2 and about 20.

The flame-retardant blends of this invention consist essentially of a blend of (a) a thermoplastic polymer, (b) between about 1-30 percent by weight of blend of the oligomer defined above, and (c) between about 1-15 percent by weight of blend of a metal oxide, such as ferric oxide, antimony oxide, or zinc ferrite, which enhances flame-retardancy of the resin.

DESCRIPTION OF THE INVENTION

The oligomers of this invention are prepared by reacting an aromatic diol of the formula HO—R—OH wherein R is as previously defined with a brominated compound of the formula

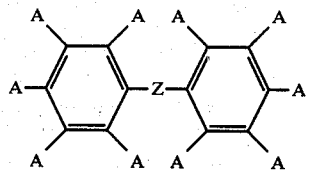

wherein each A is defined above, and Z is defined as above.

The aromatic diols employed in preparing the oligomers are diols containing at least one aromatic nucleus, i.e., the R group in the formula HO—R—OH is an arylene group, i.e., the —OH groups are attached directly to an aryl nucleus. For example, the group may be phenylene, biphenylene, naphthalene, or two aromatic benzene rings separated by an alkylidene group, e.g.,

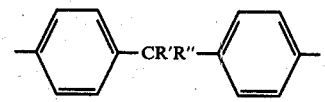

where each R' or R" can separately be hydrogen or lower alkyl (1-6 carbon atoms). Other bridging groups, such as defined by Z in the formula of the oligomers, may be used in place of the —CR'R"— to connect the two aromatic rings. Representative diols include resorcinol, "Bisphenol A" (2,2-bis-(p-hydroxy phenyl)propane), hydroquinone, 4,4'-biphenol, 4,4'-dihydroxybenzophenone, 4,4'-dihydroxydiphenyl sulfone and the like. Resorcinol and "Bisphenol A" are preferred.

Representative brominated compounds employed preparing the oligomers include decabromodiphenyl ether, decabromodiphenyl sulfide, and octabromodiphenyl ether.

The process for preparing the oligomers is preferably carried out in a solvent for at least one and preferably both the monomers. Suitable solvents include dimethyl acetamide, dimethyl formamide, dimethyl sulfoxide, N-methyl pyrrolidone, tetramethylene sulfone, and hexamethylphosphoramide, which may be used alone or in combination with an aromatic solvent such as benzene, toluene, xylene, chlorobenzene, or o-dichloro-benzene.

The reaction mixture is maintained at a temperature between about 25° and about 250° C. For convenience, reflux temperature can be employed. Pressure is not critical and super- or sub-atmospheric pressure can be used, but conveniently atmospheric pressure is employed. The oligomers are usually prepared by reacting substantially equimolar portions of the aromatic diol and brominated compound, although slight excesses of either component can be used to limit molecular weight. Generally, the brominated compound and the aromatic diol will be present in the solvent or solvent mixture in amounts of between 10 and 300 grams per liter of solvent. Time of reaction is not critical but generally ranges from 1-8 hours.

Suitable bases used to carry out the reaction include alkali metal, alkaline earth, or quaternary ammonium hydroxides or salts of weak acids, such as potassium carbonate, sodium carbonate, magnesium oxide, sodium hydroxide, potassium hydroxide and calcium hydroxide. Besides in sutu contacting of the aromatic diol with the base, a pre-prepared salt of the formula M—O—R—O—M where M is an akali metal, alkaline earth metal, or quaternary ammonium ion and R has the meaning defined above, may be used directly.

If desired, the oligomer may be capped with phenol or a similar compound to improve thermal stability. Alternatively, the reaction can be terminated with methyl chloride or ethyl bromide or the like to provide stable alkyl ends on the oligomer. At the end of the reaction, the oligomer is precipitated by adding the reaction mixture to a nonsolvent for the oligomer, such as methanol. The precipitate is then collected and dried.

To prepare the flame-retardant blends of this invention, the oligomer and the thermoplastic polymer are blended by mixing them by any convenient means. As previously mentioned, the oligomer is added in amounts of between 1 and 30 percent based on total weight, and preferably between 10 and 25 percent.

A metal oxide enhances the flame-retardant nature of the blends and the blends of this invention contain between about 1-15 percent, preferably 3-10 percent, by weight based on total weight, of a metal oxide. Preferred metal oxides include antimony oxide, iron oxide, zinc oxide, zinc ferrite and the like. The particular metal oxide selected is one that is compatible with the thermoplastic polymer, i.e., it does not tend to degrade the polymer employed.

Thermoplastic polymers useful in this invention include polyesters, such as polyethylene terephthalate or polybutylene terephthalate; or polyamides such as polyhexamethylene adipate or polycaprolactam, or polycarbonates, such as prepared by the reaction of 2,2-bis-(p-hydroxyphenyl) propane with carbonyl chloride. The polymers are high polymers of film-forming molecular weight. The polymers can be copolymers such as nylon 66/6 or can be physical blends of polyamides, or polyesters or polycarbonates. Preferably, the polymer is a polyamide including copolyamides or mixtures of polyamides.

The polyamides are well known in the art and are of film-forming molecular weight. The polyamide resin can be produced by condensation of equimolar amounts of a saturated organic dicarboxylic acid containing from 4-12 carbon atoms with an organic diamine containing 2-13 carbon atoms, in which the diamine can be employed, if desired, to provide an excess of amine end groups over carboxyl end groups in the polyamide or, vice versa, an excess of diacid can be used. Equally well, these polyamides may be made from amine-forming and acid-forming derivatives of said amines and acids such as esters, acid chlorides, amine salts, etc. Representative dicarboxylic acids used to make the polyamides include adipic acid, pimelic acid, suberic acid, sebacic acid, and dodecanedioic acid, while representative diamines include hexamethylenediamine and octamethylenediamine. In addition, the polyamide may be prepared from self-condensation of a lactam. Examples of polyamides include polyhexamethylene adipamide (66 nylon), polyhexamethylene azelaamide (69 nylon), polyhexamethylene sebacamide (610 nylon), and polyhexamethylene dodecanoamide (612 nylon), polybis-(4-aminocyclohexyl)methane dodecanoamide, or the polyamides produced by ring opening of lactams, i.e., polycaprolactam (6 nylon), polylauryl lactam, or poly-11-aminoundecanoamide. It is also possible to use polyamides prepared by the copolymerization of two of the above polymers or terpolymerization of the above polymers or their components, as for example, a polymer made of adipic acid, and isophthalic acid and hexamethylene diamine. Blends of polyamides, such as a mixture of 66 nylon and 6 nylon are also included. Preferably the condensation polyamide employed herein is polyhexamethylene adipamide (66 nylon).

Fillers are reinforcing agents such as glass fibers, graphite fibers, mica, wollastonite, aluminum silicate, etc., may be used in the polymer composition to modify properties such as stiffness and toughness. Pigments can also be used.

In the Examples which follow thermal stability of the blends obtained therein was determined by measuring the melt index (a measurement that provides a number which is a function of the molecular weight of the thermoplastic polymer in the resin—the higher the melt index the lower the molecular weight of the polymer measured) in a standard melt index appraratus as a function of time using ASTM method D1238-73. The apparatus had a 0.0823 inch (2.09 mm) orifice and a 2170 g weight was used to force the polymer through the orifice at a temperature of 280° C. or 300° C.

Tensile strength and elongation measurements were measured as described in ASTM D638-77a except that 3 specimens rather than 5 were tested and samples were not conditioned at 50% relative humidity, but, rather, were tested dry as molded (DAM) after conditioning for 24 hours under nitrogen at 23° C.

Flexural modulus was measured as described in ASTM D790-71 except that 3 rather than 5 specimens were tested and conditioning was carried out for 24 hours under nitrogen at 23° C. (DAM).

Notched Izod values were determined by the procedure described in ASTM D256-73. Samples were tested dry as molded (DAM) after conditioning for 24 hours under nitrogen at 23° C.

EXAMPLE 1

A. Preparation of oligomer

An oligomer was prepared by heating 33.0 grams (0.30 mole) resorcinol with 300 grams (0.313 mole) decabromodiphenyl ether (DBDPE) in 600 ml chlorobenzene and 600 ml dimethyl acetamide (DMAC). 27 grams of sodium hydroxide flake was added as the base required to carry out the reaction. The mixture was heated at reflux (146° C.) for 3 hours and water formed by the reaction was removed using a modified Dean Stark trap. The reaction mixture was filtered hot and the oligomer was precipitated by pouring the reaction mixture into 3 liters of methanol. The solid product was collected and dried. Oligomer recovered was 194 grams. The oligomer had an inherent viscosity of 0.032 dl/g when measured at 0.5 g/100 ml chlorobenzene at 30° C. The number average molecular weight of the product was 2770 as measured by vapor pressure osmometry in o-dichlorobenzene at 100° C.

B. Preparation of polyamide composition

1. A flame-retardant polyamide resin composition was prepared by mixing 5% zinc ferrite and 12% of the oligomer prepared in part A with a 90%/10% 66/6 polyamide copolymer having an intrinsic viscosity above 1.0 in a Brabender mixer for 5 minutes at 260° C. Samples of the resin were molded into 1/16" bars at 270° C. and 11 MPa (1600 psi) pressure, and tested for flammability by UL Test 94. The samples were found to have a flammability rating of V-O by this test and an average burn time of 3.8 seconds.

2. Melt index values of an additional composition of the oligomer in 66 nylon having an intrinsic viscosity above 1.0 were obtained at 5 minute intervals so that the progressive degradation of polymer at 280° C. could be obtained. As shown by the data below, the flame-retardant polyamide resin was more thermally stable than a similar polyamide resin containing decabromodiphenyl ether (DBDPE), a known flame-retardant, in place of the oligomer.

| Bromine Compound | DBDPE | Resorcinol-DBDPE Oligomer |
|---|---|---|
| Composition |  |  |
| Amount of Bromine Compound | 2.0 g | 2.4 g |
| Wt. % Bromine in Composition | 8.3% | 8.4% |
| $ZnFe_2O_4$ | 1.0 g | 1.0 g |
| 66 Nylon | 17.0 g | 16.6 g |
| Melt Index (g/min. at 280° C.) |  |  |
| After 5 mins. | 4.62 | 3.23 |
| After 10 mins. | 13.8 | 2.04 |
| After 15 mins. |  | 2.12 |

EXAMPLE 2

Preparation of oligomer

A. An oligomer was prepared by heating 2000 grams (2.085 moles) decabromodiphenyl ether with 476 grams (2.085 moles) 2,2-bis-(p-hydroxyphenyl) propane in 4.0 liters of N,N-dimethyl acetamide and 4.0 liters of monochlorobenzene. Sodium hydroxide flake (175 g) was added as the base required to carry out the reaction. The reaction was heated under nitrogen at reflux (146° C.) for four hours while removing the water produced with a modified Dean Stark trap. Sodium bromide was filtered off. The oligomer was precipitated in methanol, washed with methanol, and dried in a vacuum oven. The oligomer had an inherent viscosity of 0.02 dl/g at 0.5 g/100 ml chlorobenzene at 30° C. 12.0 g of the oligomer, 4.8 g antimony trioxide, and 43.2 g of a 66 nylon having an intrinsic viscosity above 1.0 and a number average molecular weight of about 18,000 were compounded in a Brabender mixer for 10 minutes at 270° C. The sample was compression molded at 275° C. into a 1.6 mm × 12.7 mm × 127 mm bar and tested for flammability by the procedure of UL 94, except 3 rather than 5 bars were tested. The sample was rated V-O and had an average burn time of 0.2 seconds.

B. When the mixture of part A was used except that 30.2 g of the 66 nylon were used and 13.0 g of 1/16" glass fibers were added, and was compression molded at 275° C. into 1.6 mm × 12.7 mm × 127 mm bars and tested for flammability by UL 94, using 3 bars rather than 5 bars as specified, the sample was rated V-O and had an average burn time of 0.0 seconds.

Intrinsic viscosity of the nylons used herein was determined in 90% formic acid at 25° C.

EXAMPLE 3

A. Preparation of oligomer

A resorcinol-decabromodiphenyl ether oligomer was prepared by heating 16.5 grams (0.15 mole) resorcinol with 143.9 grams (0.15 mole) decabromodiphenyl ether (DBDPE) in 300 ml chlorobenzene and 300 ml dimethyl acetamide (DMAC). 30 g of anhydrous potassium carbonate was also added as the base required to carry out the reaction. The mixture was heated at reflux (146° C.) for 5 hours and water formed by the reaction was removed using a modified Dean Stark trap. The reaction mixture was filtered hot and the oligomer was precipitated by pouring the reaction mixture into 2 liters of methanol. The solid product was collected and dried. Oligomer recovered was 105 grams.

B. Preparation of polyester composition

The resorcinol-decabromodiphenyl ether (DBDPE) oligomer was used to prepare a flame-retardant polyethylene terephthalate (PET) composition having an inherent viscosity over 0.4 and containing 5% $Sb_2O_3$ and 10% resorcinol-DBDPE oligomer. The composition was rated V-O in 1/16" section by UL Test 94 and had zero average burn time.

Thermal stability of the above composition was compared with a similar one containing DBDPE rather than the oligomer. As shown below, the oligomer-containing composition was substantially more stable at 280° C. than the composition containing DBDPE.

| Bromine Source Composition | DBDPE | Resorcinol-DBDPE Oligomer |
|---|---|---|
| $Sb_2O_3$ | 1.0 g | 1.0 g |
| Bromine Compound | 2.0 g | 2.0 g |
| PET | 17.0 g | 17.0 g |
| Melt Index (g/min. at 280° C.) |  |  |
| After 5 mins. | 3.78 | 2.79 |
| After 10 mins. | 8.77 | 4.90 |

EXAMPLE 4

A. Preparation of oligomer 750 g decabromodiphenyl ether (0.78 mole) and 178.5 grams (0.78 mole) of 2,2-bis-(p-hydroxyphenyl) propane were placed in a 4 liter resin kettle along with 1.5 liter dimethyl acetamide and 1.5 liter chlorobenzene. The mixture was stirred and heated under nitrogen to 130° C. Then, 33.3 g of sodium hydroxide was added and the mixture was refluxed for 1 hour at 146° C. Then, an additional 33.3 g of sodium hydroxide was added. The mixture was refluxed at 146° C. for a total of 4 hours while the water of reaction was continually removed with a modified Dean Stark trap. At the end of this time the solution was filtered hot to remove sodium bromide and the oligomer was precipitated by pouring the filtered reaction solution into 4 liters of rapidly stirred methanol. The precipitate was thoroughly washed with methanol, collected by filtration, and dried. The weight of dried product was 688 grams. The inherent viscosity of the product was 0.04 dl/g when measured at 0.5 g/100 ml chlorobenzene at 30° C. The number average molecular weight was determined to be 4110, by vapor pressure osmometry in o-dichlorobenzene at 100° C.

B. Preparation of polyamide composition

The oligomer was compounded with 66 nylon having an intrinsic viscosity over 1.0 at 288° C. melt temperature in a 28 mm twin screw extruder to give a composition containing 5% (wt.) zinc ferrite and 15% (wt.) of the oligomer. The resulting composition was extruded into strands and chopped into pellets. The pellets were used to measure melt index at 300° C. and were injection molded to give test bars for flammability testing by UL 94. For comparison purposes 66 nylon was compounded with 5% (wt.) zinc ferrite and 12% decabromodiphenyl ether and injection molded in a similar manner. Results obtained with the two compositions are shown in the data below which demonstrates that the oligomers prepared in this example gave a much more thermally stable composition than decabromodiphenyl ether.

| Bromine Source | 15% Example 5 Oligomer | 12% Decabromo-diphenyl Ether |
|---|---|---|
| Bromine Content (wt. %) | 9.3% | 10.0% |
| UL 94 Test | | |
| Burn Time (seconds) | 3.8 | 2.8 |
| Rating | V-O | V-O |
| Melt Index at 300° C. (g/min.) | | |
| After 5 mins. | 2.60 | 83 |
| After 10 mins. | 3.57 | — |
| After 15 mins. | 6.75 | — |

I claim:
1. A flame-retardant blend consisting of
   (a) a thermoplastic, film-forming polyamide
   (b) between about 1-30 percent by weight based on blend of an oligomer represented by the formula

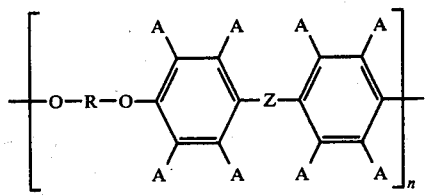

wherein R is a divalent arylene group of between about 6-15 carbon atoms; each A is independently hydrogen or bromine with the proviso that at least 6 of the A groups are bromine; n is a cardinal number of between about 2 and about 20; and Z is O, S,

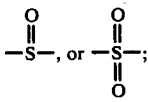

(c) and between about 1-15 percent by weight based on blend of a metal oxide synergist that does not substantially degrade the polymer.
2. The blend of claim 1 wherein in the thermoplastic film-forming polymer is polyhexamethylene adipamide.
3. The blend of claim 1 wherein the thermoplastic film-forming polymer is a mixture of polyhexamethylene adipamide and polycaprolactam.
4. The blend of claim 1 which contains a filler or a reinforcing agent.
5. The blend of claim 1 which contains glass fibers.

* * * * *